(12) United States Patent
Romero et al.

(10) Patent No.: US 8,822,536 B2
(45) Date of Patent: Sep. 2, 2014

(54) DIETARY SUPPLEMENTS CONTAINING TERPENOID ACIDS OF MASLINIC ACID OR OLEANOLIC ACID AND PROCESS FOR ENHANCING MUSCLE MASS IN MAMMALS

(71) Applicant: FHG Corporation d/b/a Integrity Nutraceuticals, Spring Hill, TN (US)

(72) Inventors: Augustin T. Romero, Spring Hill, TN (US); Tim Romero, Sarasota, FL (US); Peter J. Miller, Broomfield, CO (US)

(73) Assignee: FHG Corporation, Columbia, TN (US)

( * ) Notice: Subject to any disclaimer, the term of this patent is extended or adjusted under 35 U.S.C. 154(b) by 0 days.

(21) Appl. No.: 13/654,813

(22) Filed: Oct. 18, 2012

(65) Prior Publication Data

US 2013/0046018 A1    Feb. 21, 2013

Related U.S. Application Data

(63) Continuation of application No. 12/702,726, filed on Feb. 9, 2010, now abandoned.

(60) Provisional application No. 61/151,369, filed on Feb. 10, 2009.

(51) Int. Cl.
| | | |
|---|---|---|
| *A61K 31/19* | (2006.01) | |
| *A61K 38/00* | (2006.01) | |
| *A61K 31/70* | (2006.01) | |
| *A61K 36/00* | (2006.01) | |

(52) U.S. Cl.
USPC ............... 514/557; 514/1.1; 514/22; 424/725

(58) Field of Classification Search
None
See application file for complete search history.

(56) References Cited

U.S. PATENT DOCUMENTS

| | | | |
|---|---|---|---|
| 5,026,559 A | 6/1991 | Eichel et al. | |
| 5,096,714 A | 3/1992 | Kuhrts | |
| 5,229,131 A | 7/1993 | Amidon et al. | |
| 6,824,811 B2 | 11/2004 | Fritsche et al. | |
| 2004/0166181 A1 | 8/2004 | Hegenauer et al. | |

FOREIGN PATENT DOCUMENTS

| | | |
|---|---|---|
| EP | 1666884 A1 | 6/2006 |
| GB | 2404194 A | 1/2005 |
| WO | 2007/109370 A2 | 9/2007 |

OTHER PUBLICATIONS

Liu (1995) J. Ethnopharmacology 49: 57-68.*
Fernandez-Navarro et al. (2008) Comparative Biochem. Physiol., Part C 147: 158-167.*
Website document entitled: "Olikem: Maslinic Acid". Available at http://www.olikem.com/products/4/Maslinic-Acid.htm. (Downloaded from website Aug. 5, 2013).*
Pollier et al. (2012) Phytochemistry 77, 10-15.*
Website document entitled: "Olikem: Maslinic Acid". Archived to Oct. 8, 2010. Available at http://www.olikem.com/products/4/Maslinic-Acid.htm. (Downloaded from website Aug. 5, 2013).*
Nuno Bandeira et al.; Protein Identification by Spectral Networks Analysis; Department of Computer Science and Engineering; PNAS; vol. 104; No. 15; Apr. 2007; pp. 6140-6145.
John R. Barr et al.; Isotope Dilution-Mass Spectrometric Quantification of Specific Proteins: Model Application with Apolipoprotein A-I; Clinical Chemistry; 42:10; pp. 1676-1982, (1996).
Donald S. Kirkpatrick et al.; The Absolute Quantification Strategy: A General Procedure for the Quantification of Proteins and Post-Translational Modifications; Science Direct; Methods 35; (2005); pp. 265-273.
Hugh Wiltshire et al.; Development of a High-Performance Liquid Chromatographic-Mass Spectrometirc Assay for the Specific and Sensitive Quantification of Ro 64/0802, an Anti-Influenza Drug, and its Pro-Drug, Oseltamivir, in Human and Animal Plasma and Urine; Journal of Chromatography B, 745 (2000); pp. 373-388.
Viveka Mayya et al.; Absolute Quantification of Multisite Phosphorylation by Selective Reaction Monitoring Mass Spectrometry; Determination of Inhibitory Phosphorylation Status of Cyclin-Dependent Kinases; Molecular & Cellular Proteonics 5.6; pp. 1146-1157, 2006.
Bethny Morrissey et al.; Antigenic Characterisation of H3N2 Subtypes of the Influenza Virus by Mass Spectrometry; Journal of Virological Methods 145; (2007); pp. 106-114.
Stuart J. Rodda et al.; The Single Radial Immunodiffusion Assay Highlights Small Antigenic Differences Among Influenza Virus Hemagglutinins; Journal of Clinical Microbiology; vol. 14, No. 5; Nov. 1981, pp. 479-482.
Alejandro Wolf-Yadlin et al; Multiple Reaction Monitoring for Robust Quantitative Proteomic Analysis of Cellular Signaling Networks; Biological Engineering Division and Center for Cancer Research; Massachusetts Institute of Technology, Cambridge, MA; PNAS; vol. 104; No. 14, 2007.
Nuno Bandeira; Protein Identification by Spectral Networks Analysis; Department of Computer Science and Engineering; PNAS; vol. 104; No. 15; Apr. 2007; pp. 6140-6145.

* cited by examiner

*Primary Examiner* — Chris R Tate
*Assistant Examiner* — Russell Fiebig
(74) *Attorney, Agent, or Firm* — Gifford, Krass, Sprinkle, Anderson & Citkowski, P.C.

(57) ABSTRACT

A process for increasing lean body mass in a mammalian subject is provided that includes administering to the subject a purified quantity of maslinic acid, oleanolic acid, or a combination thereof. The administration can be orally and benefits from ingestion of an amino acid source such as dietary protein, oligopeptides, or amino acids. Administration within 2 hours of muscle-degrading exercise or on a daily basis for a period of time increases lean body mass.

4 Claims, No Drawings

DIETARY SUPPLEMENTS CONTAINING TERPENOID ACIDS OF MASLINIC ACID OR OLEANOLIC ACID AND PROCESS FOR ENHANCING MUSCLE MASS IN MAMMALS

CROSS-REFERENCE TO RELATED APPLICATION

This application is a continuation of U.S. patent application Ser. No. 12/702,726, which claims priority of U.S. Provisional Patent Application Ser. No. 61/151,369 filed Feb. 10, 2009, each of which is incorporated herein by reference.

FIELD OF THE INVENTION

The present invention relates to dietary supplement compositions containing maslinic acid and methods of enhancing nitrogen balance and lean body mass in humans and other mammals through administration thereof.

BACKGROUND OF THE INVENTION

Proteins in the body are continuously degraded and synthesized by processes that require energy. In a body, a positive nitrogen balance occurs when the total nitrogen excreted in the urine, feces and sweat is less than the total nitrogen ingested. This positive nitrogen balance must exist for new tissue to be synthesized.

Most Americans consume a 12 weight percent protein diet, while most bodybuilders consume upwards of a 25% to 30% protein diet. This bodybuilding subgroup, in order to add lean body mass to their body, must consume additional amounts of protein in order to maintain a positive nitrogen balance so the body can generate new tissue. The average sedentary adult, however, only needs to consume on the order of 30 to 60 grams of dietary protein per day to balance amino acids consumed by the body, assuming a normal caloric intake. Factors associated with increased protein requirements include the following: growth of skeletal tissue or growth during puberty, etc., low calorie diets, endurance training, strength training, high muscle-to-fat ratio, and vegetarian diets.

If protein requirements of the body are not met by dietary sources, a nitrogen deficit may develop. This deficit results from urinary nitrogen excretion exceeding the amounts of dietary protein being consumed. The increase in urinary nitrogen excretion is caused by catabolism of proteins to provide the essential amino acids that are not being supplied by dietary sources. A negative nitrogen balance is caused by: the consumption of an insufficient quantity of essential amino acid containing protein or the consumption of protein lacking essential amino acids. In addition to appropriate quantity and quality of protein consumed, sufficient energy must also be consumed to support protein metabolism, else a negative nitrogen balance will develop regardless of the quality or quantity of protein consumed.

The most recent indications are that dietary protein in excess of the current recommended dietary allowance (0.8 grams of protein per kilogram of body weight per day) is likely needed for optimal muscle growth. The current recommended daily allowance is also inadequate for an athlete who trains daily, is still growing, and/or who is in a peak performance training regime. Indeed, the benefit of increased levels of dietary protein appears to plateau at intakes well below the levels typically consumed by many athletes. Therefore, while a diet high in protein is beneficial for muscle growth, it may only be beneficial to an extent. Once a certain intake level is reached, additional protein intake does not help build muscle mass. Little progress has been made in overcoming this maximal protein intake plateau through dietary modifications.

Maslinic acid (2-α,3-β-dihydroxyolean-12-en-28-oic acid) and structurally related oleanolic acid (3-β-hydroxyolean-12-en-28-oic acid) are widely distributed in plants. These pentacyclic tri-terpenoid acids (hereafter "PTAs") are particularly abundant in the surface wax on the fruits and leaves of olive trees (*Olea europaea*) (Bianchi et al., *Phytochem.*, 37(1), pp. 205-207, 1994) and solid waste from olive oil production (García-Granados et al., *J. Chem. Res.;* 2000 (2) pp. 56-57). Loquat fruit (*Eriobotrya japonica*) also has considerable quantities of these terpenoid acids.

Maslinic acid has been studied as it relates to cell-growth changes in the liver and white muscle in different situations due to differences in protein turnover rates and nucleic acid concentrations (Peragón et al., *Comp. Biochem. Physio. Part C: Toxicology,* 147(2), pp. 158-167, 2008). These terpenoid acids have been implicated as protease inhibitors that may suppress cancers yet promote astrocytic tumors (Martin et al., *Can. Res.,* 67, pp. 3741, 2007).

Dietary maslinic acid induces higher protein synthesis in trout to sustain the generation of new cells and to be exported for different purposes. At the same time, maslinic acid stimulated the protein degradation rate, both in relative (KD) and absolute (AD) terms. The protein-efficiency ratio (PER) and feed-efficiency ratio (FER) both increased in trout fed maslinic acid concentration at 250 mg kg-1, with respect to a control. (Peragón et al., *Can. J. Fish Aquat. Sci.,* 55(3), pp. 649-659 (1998).

The presence of abundant and well-organized rough endoplasmic reticula as seen by electron microscopy in the hepatocytes of trout fed 250 mg kg-1 maslinic acid confirms the prolific biosynthesis of exportable proteins. (Ibid.) The higher number of white-muscle cells, mediated by increase in the DNA, RNA, and protein content, seems to result from a stimulation of the biosynthesis pathways of all this macromolecules similar to those produced by a growth factor. Maslinic acid fed to trout at 25 and 250 mg kg-1 increased the protein-synthesis rate (KS and AS), while no significant changes were found in fractional protein-degradation rate (KD) and only a minor increase in the absolute protein-degradation rate (AD). These changes in protein-turnover rates explain the high protein-accumulation rates (KG and AG) found in trout fed with maslinic acid. (Ibid.) Conflicting studies found 80 mg kg-1 to retard juvenile dentex fish growth (Hidalgo et al., *Aquacult. Nutri.,* 12(4), pp. 256-266, 2006).

In relation to these results, it has been reported that maslinic acid leads to a high accumulation of glycogen in rainbow trout liver (Fernández-Navarro et al., 2006) and can also act as a new type of glycogen phosphorylase inhibitor (Wen et al., 2005; 2006), the enzyme responsible for glycogen degradation in liver and white muscle.

Thus, there exists a need for a dietary supplement containing PTAs to promote building of muscle mass in a high protein content diet.

SUMMARY OF THE INVENTION

A process for increasing lean body mass in a mammalian subject is provided that includes administering to the subject a purified quantity of maslinic acid, oleanolic acid, or a combination thereof. The administration can be orally and benefits from ingestion of an amino acid source such as dietary protein, oligopeptides, or amino acids. Administration within 2 hours of muscle-degrading exercise or on a daily basis for a period of time increases lean body mass.

DETAILED DESCRIPTION OF THE PREFERRED EMBODIMENTS

The present invention has utility as a dietary supplement for increasing muscle mass in a mammalian subject. While the specific mechanism in the mammalian subject is unknown, an inventive supplement when administered to a mammalian subject allows additional consumed protein to help build muscle mass relative to a control not consuming an inventive dietary supplement. It is noted that other pentacyclic tri-terpenoid acids do not exhibit the effects of an inventive dietary supplement. As this class of compounds includes a variety of compounds identified in plant signaling, there are numerous identified pentacyclic tri-terpenoid acids. Other pentacyclic tri-terpenoid acids known illustratively include ursolic acid, boswelic acid, and tormatic acid.

Maslinic acid has an alpha ring hydroxyl group at the two position relative to a hydrogen at that position in oleanolic acid. Owing to the structural similarity therebetween, and commonality in natural sources, it has been found that maslinic acid, oleanolic acid, or a combination thereof is operative in the present invention to increase muscle mass in a mammalian subject, especially in instances when the mammalian subject is metabolically active and working muscles and simultaneously consuming a high protein diet.

According to the present invention, a mammalian subject is defined to include a horse, cow, pig, goat, rabbit, rat, mouse, cat, dog, non-human primate, and a human.

A purified quantity of maslinic acid, oleanolic acid, or a combination thereof is extracted from various natural sources or synthetically produced. Among natural sources, numerous plants produce maslinic acid and/or oleanolic acid. As noted above, olive root, olive leaves, and loquat fruit produce maslinic and oleanolic acids in high concentration.

Regardless of the natural source, the inventive composition acids are readily extracted with polar aprotic solvents such as methylene chloride, C1-C6 alcohols, C3-C6 ketones, tetrahydrofuran, formamid, C3-C16 esters, nitrogen-containing heterocyclics, and combinations thereof. In particular, it is appreciated that crude extraction from macerated plant material in a first solvent followed by a secondary extraction from the inventive acid-containing fraction serves to further purify the inventive acids. A methylene chloride initial extraction followed by a methanol extraction is exemplary of such extraction processes (Juan et al., *J. Nutri.*, 136, p. 2554, first column, ¶¶1-2, 2006).

As used herein, a "purified quantity" with respect to an inventive acid of maslinic acid, oleanolic acid, or a combination thereof is defined as being substantially free of lignins, alkaloids, cellulosic material, and plant enzymes operating on maslinic acid or oleanolic acid as enzymatic substrates. It is noted that a given quantity of inventive acid is more effective upon being administered in a purified quantity relative to consumption of an equivalent inventive acid containing amount of olive fruit. Without intending to be bound to a particular theory, plant polymeric materials such as lignins and cellulosic material tend to bind the inventive acids. The resulting extract in a biocompatible solvent is readily administered as an elixir, aqueous solution, slurried with protein or other additives, or lyophilized to a powder. Regardless of the form of a purified inventive acid, the inventive acid is readily formulated in a pharmaceutical dietary supplement formulation in solid, semi-solid, or liquid dosage forms, such as, for example, tablets, chewables, suppositories, pills, capsules, powders, liquids, or suspensions, and may be provided in unit dosages suitable for a single administration. Time release preparations are also contemplated as effective dosage formulations as detailed in the art. For example, time release formulations are provided in U.S. Pat. No. 5,096,714; U.S. Pat. No. 5,229,131; and U.S. Pat. No. 5,026,559. The compositions may include an effective amount of a selected substrate in combination with a pharmaceutically acceptable carrier and, in addition, may include other medicinal agents, pharmaceutical agents, carriers, or diluents.

In a solid composition embodiment, conventional nontoxic solid carriers may include, for example, pharmaceutical grades of mannitol, lactose, starch, magnesium stearate, sodium saccharine, talc, cellulose, glucose, sucrose and magnesium carbonate. Liquid pharmaceutically administrable compositions may, for example, be prepared by dissolving or dispersing an active compound with optimal pharmaceutical adjuvants in an excipient, such as water, saline, aqueous dextrose, glycerol, or ethanol, to form a solution or suspension. For example, the pharmaceutical composition may contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art. (*Remington's*, 20$^{th}$ edition, pp. 721-979, 2000).

In an oral administration embodiment, fine powders or granules may contain diluting, dispersing, or surface active agents. The fine powders or granules may be presented in water or in syrup, in capsules or sachets in the dry state, or in a nonaqueous solution or suspension. Suspending agents may also be included in tablets, which may include binders and lubricants in a suspension. Flavoring, preserving, suspending, thickening, or emulsifying agents may be also included to modify the taste and texture of the composition. The tablets and granules provided for oral administration may further be coated for ease of digestion. (*Ibid.*, pp. 858-902).

Preferably, the inventive acid dietary supplement composition is combined with one or more protein sources. Such sources may include whey protein isolate, whey protein concentrate, free form amino acids, buckwheat protein, soy protein isolate or concentrate, milk protein isolate or concentrate, micellar casein, calcium or other caseinate proteins, rice protein, or any combination of the above. More preferably the protein contains quantities of essential amino acids.

It is further contemplated that variable dosing regiments are operative in the method of treatment. While in some instances a single dose treatment may be effective in producing therapeutic effects, in other instances a treatment period in the range of, for example, 6 weeks to 3 months may be utilized. The composition may be administered orally, parentally, or intravenously by intramuscular, intraperitoneal, or transdermally injection. Injectables may be prepared in conventional forms, either liquid solutions or suspensions, solid forms suitable for solution or prior to injection, or as suspension in liquid prior to injection or as emulsions. The dose of the dietary supplement composition may vary depending on the age, weight, general condition of the user. For example, human 65 kg male dosage is in the range of 0.1-5,000 mg of equivalent of dry maslinic acid or oleanolic acid per day may be an effective range. Preferred doses for a human 65 kg male range from 10 to 500 mg per day. Optionally, the inventive maslinic acid is present from 0.01%-5% of the dry total weight of the composition.

It is contemplated that variable dosing regiments are operative in the inventive processes. While in some instances a single dose of inventive composition as a dietary supplement, for example, may be effective in producing therapeutic effects, in other instances a treatment period in the range of, for example, 6 weeks to 3 months may be utilized. An inventive composition is optionally delivered to a subject daily, weekly, biweekly, monthly, or any subdivision therebetween or for longer periods. In some embodiments a subject ingests an inventive composition daily. Optionally, an inventive composition is delivered one, two, three, four, five, or more times per day.

The composition is optionally administered orally, parentally, or intravenously by intramuscular, intraperitoneal, or transdermally injection. Injectables may be prepared in conventional forms, either liquid solutions or suspensions, solid forms suitable for solution or prior to injection, or as suspension in liquid prior to injection or as emulsions. The dose of the dietary supplement composition may vary depending on the age, weight, general condition of the user. Several forms of administration are operable herein illustratively including ingestion, inhalation, or injection. Typical administrations are by oral ingestion. Ingestion is optionally with or without other food. In some embodiments an inventive composition is administered to a subject along with a protein rich food or within 1 hour prior or following administration illustratively by eating a protein rich food. Carbohydrate rich foods are foods that in ingestible quantities include greater than about 5 grams of protein.

In some embodiments of the inventive processes, greater amounts of the inventive composition are initially administered to the subject's diet in order to increase or enhance muscle size or strength (loading period), followed by a maintenance period during which the amounts of inventive composition are relatively decreased. The loading period optionally extends several weeks. In some embodiments a loading period is one, two, three, four, five, six or more weeks. Optionally, a loading period is from one day to six weeks or more, as well as any period therebetween as desired by either the subject, the trainer, physician, or other depending on the desired outcome and rapidity of desired results. Once a desired muscle strength, size, or endurance has been obtained, lower amounts of the inventive composition, illustratively a maintenance period, are optionally administered to the subject to maintain or improve the results. In some embodiments the inventive composition is administered to a subject immediately following an exercise period. On non-workout days, the inventive composition is optionally administered anytime during the day, illustratively, upon awakening or otherwise during the morning hours.

The following tables are intended to illustrate a particular embodiment of the invention and are not intended to limit the scope of the appended claims, in any way.

TABLE 1

| Powder | |
| --- | --- |
| 10% by wt. maslinic acid extract | 50 mg (5 mg maslinic acid) |
| Whey Protein Isolate | 40 g |
| Natural Flavors | 200 mg |
| Thickening agents | 100 mg |
| Sucralose | 50 mg |

TABLE 2

| Powder | |
| --- | --- |
| 10% by wt. maslinic acid extract + 3% by wt. oleanolic acid | 200 mg (20 mg maslinic acid, 6 mg oleanolic acid) |

TABLE 2-continued

| Powder | |
| --- | --- |
| L-Leucine | 4000 mg |
| L-Isoleucine | 2000 mg |
| L-Valine | 2000 mg |
| Flavors | 400 mg |
| Citric Acid | 250 mg |
| Sucralose | 50 mg |

TABLE 3

| | |
| --- | --- |
| Maslinic acid | 100 mg |
| Whey Protein Isolate | 30 g |
| Whey Protein Concentrate | 5 g |
| Calcium Caseinate | 5 g |
| Aminogen | 1000 mg |
| L-Glutamine | 1000 mg |
| Flavors | 500 mg |
| Thickening Agents | 500 mg |
| Dextrose | 30 g |

TABLE 4

| | |
| --- | --- |
| Oleanolic acid | 500 mg |
| Maslinic acid | 700 mg |
| Whey Protein Isolate | 30 g |
| Whey Protein Concentrate | 5 g |
| Calcium Caseinate | 5 g |
| Aminogen | 1000 mg |
| L-Glutamine | 1000 mg |
| Flavors | 500 mg |
| Thickening Agents | 500 mg |
| Dextrose | 30 g |

The present invention is further detailed with respect to the following nonlimiting examples. These examples are not intended to limit the interpretation or scope of the appended claims.

EXAMPLE 1

The inventive composition of Table 1 is administered in a double-blind study to a group of 6 body builders, with 4 body builders acting as negative controls. Each subject consumed a diet composed of between 25 and 30 total weight percent protein with the controls receiving the composition provided in Table 1 with the exception of the maslinic acid extract. The compositions are administered once daily for 6 weeks. The test subjects at the end of the trial show a 2% increase in lean body mass relative to the control group.

EXAMPLE 2

The trial of Example 1 is repeated with the inventive composition of Table 2 substituted for that of Table 1 while a repeat study control group received the Table 2 formulation lacking inventive acid with a comparable result to that of Example 1.

EXAMPLE 3

The procedure of Example 1 is repeated with the composition taken orally within 2 hours of completing the most strenuous exercise routine of the day with comparable results to that of Example 1.

EXAMPLE 4

The procedure of Example 1 is repeated with the inventive composition of Table 4. After 2 weeks of administration, test subjects had a lean body mass increase of 0.3% relative to controls who consumed the Table 4 composition exclusive of oleanolic acid and maslinic acid.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for increasing lean body mass in a mammalian subject in need thereof comprising:
    administering to said subject a composition comprising purified quantities of maslinic acid, and oleanolic acid, said purified quantities mixed with at least one dietary supplement additive of protein or amino acids; wherein said maslinic acid comprises 0.01%-5% of the dry weight of the composition.

2. The process of claim 1, wherein said administering is orally.

3. The process of claim 1, wherein said purified quantity is devoid of cellulosics, lignins, or alkaloids associated with a plant from which said purified quantities is derived.

4. The process of claim 1, wherein said administering occurs within 2 hours of exercise by said subject.

* * * * *